(12) United States Patent
Daly et al.

(10) Patent No.: US 9,144,536 B1
(45) Date of Patent: Sep. 29, 2015

(54) PARTICULATE ZINC OXIDE WITH MANGANESE, IRON AND COPPER DOPANT IONS

(71) Applicant: JOHNSON & JOHNSON CONSUMER INC., Skillman, NJ (US)

(72) Inventors: Susan Daly, Basking Ridge, NJ (US); Euen Thomas Graham Ekman Gunn, Hopewell, NJ (US); Yongyi Zhang, Harrison, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 8 days.

(21) Appl. No.: 14/269,416

(22) Filed: May 5, 2014

(51) Int. Cl.
*H01L 29/74* (2006.01)
*H01L 31/111* (2006.01)
*A61K 8/27* (2006.01)
*A61Q 17/04* (2006.01)

(52) U.S. Cl.
CPC . *A61K 8/27* (2013.01); *A61Q 17/04* (2013.01); *A61K 2800/26* (2013.01)

(58) Field of Classification Search
CPC .............. H01L 21/3164; H01L 21/02348; H01L 21/0257; H01L 21/31658; H01L 29/7869
USPC .............. 257/43, 148, 607, 749, 765, 771, 257/E21.006, E21.043, E21.121, E21.134, 257/E21.253, E21.329
See application file for complete search history.

(56) References Cited

U.S. PATENT DOCUMENTS

| | | | |
|---|---|---|---|
| 5,198,025 A | 3/1993 | Dausch | |
| 5,441,726 A | 8/1995 | Mitchnick et al. | |
| 5,800,824 A * | 9/1998 | Pfrommer et al. | 424/401 |
| 8,753,684 B2 * | 6/2014 | Pfluecker et al. | 424/489 |
| 2006/0104925 A1 | 5/2006 | Knowland et al. | |
| 2006/0134026 A1 | 6/2006 | Park et al. | |
| 2006/0239941 A1 * | 10/2006 | Park et al. | 424/59 |
| 2008/0031832 A1 | 2/2008 | Wakefield et al. | |
| 2012/0258154 A1 | 10/2012 | Pfluecker et al. | |

FOREIGN PATENT DOCUMENTS

WO WO 2006/058209 A 6/2006
WO WO 2006/061627 A 6/2006

OTHER PUBLICATIONS

Aydin et al., "Synthesis, diffused reflectance and electrical properties of nanocrystalline Fe-doped ZnO via sol-gel calcination technique", *Optics & Laser Technology* (2013) 48:447-452.
Feng et al., "Hydrothermal synthesis and photocatalytic performance of metial-ions doped TiO$_2$", *Applied Catalysis A: General 413-414* (2012) 238-244.
Truffault et al., "Synthesis of nano-hematite for possible use in sunscreens", *Journal of Nanoscience and Nanotechnology* (Mar. 2011) 11(3):2413-20.
Truffault et al., "Synthesis and characterization of Fe doped CeO2 nanoparticles for pigmented ultraviolet filter applications", Journal of Nanoscience and Nanotechnology (May 2011) 11(5):4019-28.

* cited by examiner

*Primary Examiner* — David Nhu

(57) ABSTRACT

A particulate metal oxide includes a cationic portion that includes a zinc portion, a first iron dopant portion and a second dopant portion consisting of manganese and copper, where the zinc portion is about 99% by weight or more of the cationic portion, and the weight percent of the second dopant portion is greater than twice the weight percent of the first iron dopant portion.

12 Claims, No Drawings

PARTICULATE ZINC OXIDE WITH MANGANESE, IRON AND COPPER DOPANT IONS

FIELD OF THE INVENTION

The invention relates to particulate zinc oxide. More specifically, the invention relates to particulate zinc oxide that has a first manganese dopant portion and a second dopant portion consisting of copper and iron.

BACKGROUND OF THE INVENTION

Skin cancer is a significant public health concern which represents 50% of diagnosed cases of cancer in the United States. Ultraviolet radiation (UV) can cause molecular and cellular level damage, and is considered the leading environmental factor responsible for skin cancer. The prolonged exposure to UV radiation, such as from the sun, can lead to the formation of light dermatoses and erythemas, as well as increase the risk of skin cancers, such as melanoma, and accelerate skin aging processes, such as loss of skin elasticity and wrinkling.

The damaging effects of UV exposure can be suppressed by topical application of sunscreens which contain compounds that absorb, reflect or scatter UV, typically in the UVA (wavelengths from about 320 to 400 nm) or UVB (wavelengths from around 290 to 320 nm) range of the spectrum. Numerous sunscreen compounds are commercially available with varying ability to shield the body from ultraviolet light.

Zinc oxide is a particulate material that is useful as sunscreen, since it absorbs and scatters ultraviolet radiation. However, the inventors have recognized that a need exists for zinc oxide having enhanced optical properties, particularly for use in sunscreens and personal care products, and more particularly for enhanced UVA absorption.

SUMMARY OF THE INVENTION

According to one aspect of the invention, a particulate metal oxide comprises a cationic portion that includes a zinc portion, a first iron dopant portion and a second dopant portion consisting of manganese and copper. The zinc portion is about 99% by weight or more of the cationic portion. The weight percent of the second dopant portion is greater twice the weight percent of the first iron dopant portion.

DETAILED DESCRIPTION OF THE INVENTION

The inventors have found that a particulate zinc oxide having certain dopants that are present in low levels and in particular ratios provides improved performance with respect to absorption in the UVA portion of the electromagnetic spectrum.

It is believed that one skilled in the art can, based upon the description herein, utilize the present invention to its fullest extent. The following specific embodiments are to be construed as merely illustrative, and not limitative of the remainder of the disclosure in any way whatsoever. Unless defined otherwise, all technical and scientific terms used herein have the same meaning as commonly understood by one of ordinary skill in the art to which the invention belongs. Unless defined otherwise, all references to percent are percent by weight. Furthermore, unless defined otherwise "substantially free of" indicates that a particular ingredient or substituent is present in an amount of about one percent by weight or less, such as less than about 0.5% by weight or less, such as less than about 0.1% by weight or less.

Particulate Metal Oxide

Embodiments of the invention relate to particulate metal oxides. By "particulate" it is meant a material that is, under ambient conditions, a finely-divided, solid material. As one skilled in the art will readily recognize, metal oxides are ionic solids, generally comprising cations (predominantly metal cations), and anions (predominantly oxygen anions) arranged in a crystalline lattice structure.

Accordingly, particulate metal oxides of the present invention comprise a cationic portion. The cationic portion comprises a zinc portion, which is the predominant cation in the particulate metal oxide. As such, the zinc portion is about 99% by weight or more of the cationic portion. According to certain embodiments, the zinc portion is about 99% to about 99.75% of the cationic portion, such as from about 99% to about 99.5%, such as from about 99% to about 99.25%.

The cationic portion further comprises a first iron dopant portion and a second dopant portion consisting of manganese and copper. As used herein, "dopant", or "dopant portion", means those cations, or portion of cations, that are intimately incorporated into the crystalline lattice structure of the metal oxide, as further described herein, thereby modifying the electronic properties of the metal oxide. One skilled in the art will recognize that the mere coating of a particulate metal oxide with a material having metal cations is not sufficient in and of itself to provide modified electronic properties of the metal oxide, since mere coating will not provide intimate incorporation of the metal cations into the crystalline lattice structure of the metal oxide.

The first iron dopant portion may be about 0.1% to about 0.75% by weight of the cationic portion. According to certain embodiments, the manganese portion is about 0.1% to about 0.6% of the cationic portion, such as from about 0.15% to about 0.5%, such as from about 0.2% to about 0.3%. Furthermore, the iron dopant portion may exist in varying oxidation states. According to one embodiment the iron exists as either $Fe^{2+}$ or $Fe^{3+}$. In one embodiment, the iron exists as $Fe^{2+}$.

The second dopant portion is present in a concentration by weight that is greater than twice the concentration by weight of the first iron dopant portion. The second dopant portion may be present in a ratio by weight to the first iron dopant portion that is at least 2.25:1, such as at least 2.5:1, such as at least 3:1.

The manganese portion and the copper portion concentration by weight in the second dopant portion may each independently be about 0.1% to about 0.75% by weight of the cationic portion. According to certain embodiments, the manganese portion and the copper portion are independently from about 0.15% to about 0.6% of the cationic portion, such as from about 0.2% to about 0.55%, such as from about 0.24% to about 0.48%. According to one embodiment, the manganese portion is greater than the copper portion.

Furthermore, the manganese portion and the copper portion may exist in varying oxidation states. According to one embodiment the manganese exists as either $Mn^{2+}$ or $Mn^{3+}$. In one embodiment, the manganese exists as $Mn^{2+}$. According to one embodiment the copper exists as either $Cu^{2+}$ or $Cu^{3+}$. In one embodiment, the copper exists as $Cu^{2+}$.

Furthermore, the sum of the first iron dopant portion and the second dopant portion may be from about 0.25% to about 1% of the cationic portion, such as from about 0.5% to about 1% of the cationic portion, such as from about 0.75% to about 1% of the cationic portion, such from about 0.85% to about 0.95% of the cationic portion.

The inventors have found that when the second dopant portion consisting of a manganese dopant and a copper dopant is present in a concentration by weight that is greater than twice concentration by weight of the first iron dopant portion, particular benefits are achieved in the intensity of absorption centered in the UVB-range. For example, the weight ratio of second dopant portion:iron dopant portion may be 3:1, the cationic portion may contain about 0.24% of iron portion and 0.72% second dopant portion. In this example, the cationic portion contains 0.24% manganese and 0.48% copper; or vice-versa.

As one skilled in the art will readily appreciate, additional cations may be present in small concentrations in the particulate metal oxide without compromising the properties thereof. For example, in certain embodiments, small concentrations of these additional cations may be collectively present in the cationic portion in concentrations of, for example, less than about 0.5%, such as less than about 0.25%, such as less than about 0.1%. According to certain embodiments, the additional cations may be collectively present in the cationic portion in a concentration from about 0.001% to about 0.25%, such as from about 0.001% to about 0.1%. The additional cations may include cations of alkali metals, alkaline earth metals; transition metals other than zinc, manganese and iron; as well as cations of metals such as gallium, germanium, gallium, indium, tin, antimony, thallium, lead, bismuth, and polonium.

Particulate metal oxides of the present invention may be made by various methods, such as methods reducing oxide ores using, for example, carbon or other suitable reducing agents, and then re-oxidizing. Other suitable methods include wet chemical methods. One example of a wet chemical method includes mixing alkaline salt solutions of the various cations and causing ZnO to precipitate by reducing the pH using an acid such as oxalic or formic acid. A particularly suitable wet chemical method is the so-called "sol-gel" method, an example of which is described below.

According to one embodiment of the invention, the particulate metal oxide formed by a method that includes combining a solvent system comprising water with a zinc salt, an iron salt, a manganese salt and a copper salt to form a salt solution. According to certain embodiments, in the salt solution, the concentration of iron cation is less than the sum of the concentration of manganese ion and copper ion.

Any of a variety of salts may be used as sources of the various cations. Examples include zinc acetate, zinc chloride, manganese chloride, manganese sulfate, manganese acetate, ferric chloride, ferric sulfate, aluminum chloride, among other salts.

Additional components may be added to the mixture of the solvent system and the salts. For example, a surfactant such as an ethanolamine (e.g. triethanolamine), as well as homogenizing and or pH adjusting agents such an alcohol and ammonia may be added as well. Suitable alcohols include ethanol, 2-methoxyethanol, and the like.

Typically, in a sol-gel process a stable, colloidal solution (sol) is formed after mixing the solvent system, the salts and the optional surfactant, and homogenizing/pH adjusting agents. Over time, a gel network comprising zinc cations, manganese cations and cations of the third salt is then gradually formed, by solidification and condensation of colloidal particles having solvent system trapped therein.

The gel network is then allowed to dry, such as at ambient temperatures, to remove at least portions of the solvent system. Then the dried gel network is then calcined, heated at high temperatures in an oxygen-containing atmosphere, to remove any remaining solvent system as well as residual organics and densify the gel network. Upon sufficient heating, the particulate metal oxide is formed. According to certain embodiments, the calcinations is performed at a temperature of at least about 400° C., such as from about 400° C. to about 1200° C., such as from about 600° C. to about 1000° C., such as about 700° C.

According to certain embodiments, the particulate metal oxides of the present invention are also characterized not only by high absorbance, but also by high Long-Short Absorbance Ratios (LSAR). "LSAR" is a measure of the relative amount of absorbance in the long wavelength UVA-I and visible region of the spectrum, which is the region of the spectrum that is typically absorbed less by conventional sunscreens, yet is still responsible for biological deleterious effects, as compared with short wavelength absorbance. This ratio of absorbance across long wavelengths to absorbance at shorter wavelengths thus provides a basis for comparing the ability of the various doped particulate metal oxides to absorb in this region of the spectrum. Long-Short Absorbance Ratio may be determined by integrating (summing) the absorbance from wavelengths ranging from 380 nm through 410 nm and dividing this by the integration (sum) of absorbance from wavelengths ranging from 340 nm through 350 nm. According to certain embodiments, the LSAR of particulate metal oxides of the present invention is about 1.5 or greater, such as about 1.7 or greater.

The following examples are illustrative of the principles and practice of this invention, although not limited thereto. Numerous additional embodiments within the scope and spirit of the invention will become apparent to those skilled in the art once having the benefit of this disclosure.

EXAMPLES

Example IA

Preparation of Inventive Examples

Inventive Example E1-E2

Zinc oxide doped with iron, manganese, and copper was prepared by a sol-gel process utilizing zinc acetate dehydrate and iron (II) chloride hexahydrate, manganese (II) chloride, and copper (II) chloride. In a 100-ml beaker, 20 ml distilled water and 30 ml triethanolamine were combined and 2 ml of ethanol was added drop-wise with continuous stirring and a visibly homogeneous solution was obtained. In another beaker, 0.5M iron (II) chloride hexahydrate was prepared (6.78 g iron chloride in 50 mL water). In a third beaker, 0.5M zinc acetate dihydrate was prepared. In another beaker, 0.5M of manganese (II) chloride was prepared. In yet another beaker, 0.5M of copper (II) chloride was prepared. The solutions were allowed to continue to stir for 2-3 hours. In a 500-ml beaker the TEA/water mixture as well as the zinc acetate solution and iron (II) chloride solution were mixed.

For Inventive Example E1, sufficient iron (II) chloride solution was added to provide 0.2375% by weight of iron cations relative to the total cationic portion (zinc plus iron plus manganese plus copper). Sufficient manganese (II) chloride solution was added to provide 0.475% of manganese cations relative to the total cationic portion. Sufficient copper (II) chloride solution was added to provide 0.2375% of copper cations relative to the total cationic portion. Accordingly, the total amount of added dopant was 0.95% percent by weight of combined iron, manganese and copper cations relative to the total cationic portion, and the ratio of added manganese:copper:iron cations was 2:1:1.

For Inventive Example E2, sufficient iron (II) chloride solution was added to provide 0.2375% by weight of iron cations relative to the total cationic portion (zinc plus iron plus manganese plus copper). Sufficient manganese (II) chloride solution was added to provide 0.2375% of manganese cations relative to the total cationic portion. Sufficient copper (II) chloride solution was added to provide 0.475% of copper cations relative to the total cationic portion. Accordingly, the total amount of added dopant was 0.95% percent by weight of combined iron, manganese and copper cations relative to the total cationic portion, and the ratio of added manganese:copper:iron cations was 1:2:1.

Comparative Example C1

Zinc oxide doped with iron, manganese, and copper was prepared by a sol-gel process using iron (II) chloride hexahydrate, manganese (II) chloride, and copper (II) chloride in a manner similar to Inventive Examples E1-E2, except that sufficient iron (II) chloride solution was added to provide 0.317% by weight of iron cations relative to the total cationic portion (zinc plus iron plus manganese plus copper). Sufficient manganese (II) chloride solution was added to provide 0.317% of manganese cations relative to the total cationic portion. Sufficient copper (II) chloride solution was added to provide 0.317% of copper cations relative to the total cationic portion. Accordingly, the total amount of added dopant was 0.95% percent by weight of combined iron, manganese and copper cations relative to the total cationic portion, and the ratio of added manganese:copper:iron cations was 1:1:1.

Comparative Example C2

Zinc oxide doped with manganese and copper was prepared by a sol-gel process in a manner similar to that described above for Inventive Examples E1-E2, except that iron (II) chloride hexahydrate was omitted. Sufficient manganese (II) chloride solution was added to provide 0.475% of manganese relative to the total cationic portion (zinc plus manganese plus copper). Sufficient copper (II) chloride solution was added to provide 0.475% of manganese relative to the total cationic portion. Accordingly, the total amount of added dopant was 0.95% percent by weight of combined manganese cations and copper ions relative to the total cationic portion.

Comparative Example C3

Zinc oxide doped with iron and copper was prepared by a sol-gel process in a manner similar to that described above for Inventive Examples E1-E2, except that manganese (II) chloride was omitted. Sufficient copper (II) chloride solution was added to provide 0.475% of manganese relative to the total cationic portion (zinc plus iron plus copper). Sufficient iron (II) chloride solution was added to provide 0.475% of manganese relative to the total cationic portion. Accordingly, the total amount of added dopant was 0.95% percent by weight of combined iron cations and copper ions relative to the total cationic portion.

Comparative Example C4

Zinc oxide doped with manganese and iron was prepared by a sol-gel process in a manner similar to that described above for Inventive Examples E1-E2, except that iron copper (II) chloride was omitted. Sufficient manganese (II) chloride solution was added to provide 0.475% of manganese relative to the total cationic portion (zinc plus iron plus manganese). Sufficient iron (II) chloride solution was added to provide 0.475% of manganese relative to the total cationic portion. Accordingly, the total amount of added dopant was 0.95% percent by weight of combined manganese cations and copper ions relative to the total cationic portion.

Example 1B

Spectrophotometric Analysis of Zinc Oxide Samples

Comparative Examples C1-C4 and Inventive Examples E1-E2 were separately dispersed to a concentration by weight of 5% in petrolatum. Furthermore, a commercially available zinc oxide, Z-Cote HP1, commercially available from BASF of Ludwigshafen, Germany, was also dispersed in petrolatum. Each of these test samples were evaluated for UV-absorbance spectrum to Vitro-Skin (available from Innovative Measurement Solutions of Milford, Conn.) and using a Labsphere 100 UV spectrophotometer (Labsphere, North Sutton, N.H., USA).

The test material was treated by spreading evenly over the Vitro-Skin using by applying 2 mg/cm$^2$ and comparing with untreated Vitro-Skin. Absorbance was measured using a calibrated Labsphere UV-1000S UV transmission analyzer (Labsphere, North Sutton, N.H., USA). For each batch of synthesized sample, this is repeated in duplicate. The absorbance measures were used to calculate sun protection factor (SPF) and absorbance at a wavelength of 350 nm.

Absorbance is calculated using the formula below, where $\lambda$ is the wavelength of 350 nm, $I_1$ is the incident intensity of electromagnetic energy at 350 nm and $I_0$ is the transmitted intensity at 350 nm.

$$A_\lambda = -\ln(I_1/I_0)$$

Absorbance intensity at 350 nm is the absorbance intensity at that particular wavelength. In vitro SPF and Absorbance Intensity at 350 nm are reported in Table 1. Where the synthesis was repeated in triplicate, standard deviation values for the in vitro SPF and Absorbance Intensity at 350 nm are also reported in Table 1.

Absorbance of Inventive Examples E1-E2 and Comparative Examples C1-C4 are shown in Table 1.

TABLE 1

| Example | Cations | Cation Ratio | Absorbance Intensity at 350 nm |
| --- | --- | --- | --- |
| Inventive Example E1 | Mn:Cu:Fe | 2:1:1 | 0.337/+0.048 |
| Inventive Example E2 | Mn:Cu:Fe | 1:2:1 | 0.271 |
| Comparative Example C1 | Mn:Cu:Fe | 1:1:1 | 0.110 |
| Comparative Example C2 | Mn:Cu | 1:1 | 0.110 |
| Comparative Example C3 | Cu:Fe | 1:1 | 0.081 |
| Comparative Example C4 | Mn:Fe | 1:1 | 0.161/+0.018 |

As shown in Table 1 above, the inventive examples are metal oxides having a cationic portion that is more than 99% zinc, where the cationic portion further comprises a first iron dopant portion and a second dopant portion consisting of manganese and copper, where the concentration of the second dopant portion is greater than twice the concentration of the first iron dopant portion. The absorbance at 350 nm of the inventive examples are 68% higher to more than double that of Comparative Example 4.

From the absorbance measurements, the relative amount of absorbance in the long wavelength UVA-I and visible region of the spectrum (the region of the spectrum that is typically absorbed less by conventional sunscreens, yet is still responsible for biological deleterious effects) as compared with short wavelength absorbance was determined. This ratio of absorbance across long wavelengths to absorbance at shorter wavelengths thus provides a basis for comparing the ability of the various doped particulate zinc oxides to absorb in this region of the spectrum. Specifically, a "Long-Short Absorbance Ratio" (LSAR) was determined for each sample by integrating (summing) the absorbance from wavelengths ranging from 380 nm through 410 nm and dividing this by the integration (sum) of absorbance from wavelengths ranging from 340 nm through 350 nm. The mean Long-Short Absorbance Ratio is reported in Table 2, and where the synthesis was conducted in triplicate, standard deviation results are also reported in Table 2 as non-zero values. The results for doped zinc oxide samples are shown in Table 2.

Long-Short Absorbance Ratio of Inventive Examples E1-E2 and Comparative Examples C1-C4 are shown in Table 2.

TABLE 2

| Example | Cations | Cation Ratio | LSAR Mean/Std Dev. |
|---|---|---|---|
| Inventive Example E1 | Mn:Cu:Fe | 2:1:1 | 1.72/0.078 |
| Inventive Example E2 | Mn:Cu:Fe | 1:2:1 | 1.51 |

The invention claimed is:

1. A particulate metal oxide comprising a cationic portion, wherein the cationic portion comprises a zinc portion, a first iron dopant portion and a second dopant portion consisting of manganese and copper, wherein the zinc portion is about 99 percent by weight or more of the cationic portion, and wherein a weight percent of the second dopant portion is greater than twice a weight percent of the iron dopant portion.

2. The particulate metal oxide of claim 1 wherein the second dopant portion is present in a ratio to the first iron dopant portion that is at least 2.25:1.

3. The particulate metal oxide of claim 1 wherein the second dopant portion is present in a ratio to the first iron dopant portion that is at least 2.5:1.

4. The particulate metal oxide of claim 1 wherein the second dopant portion is present in a ratio to the first iron dopant portion that is at least 3:1.

5. The particulate metal oxide of claim 1 wherein the weight percent of the manganese in the second dopant portion is greater than the weight percent of the copper in the second dopant portion.

6. The particulate metal oxide of claim 1 wherein the weight percent of the copper in the second dopant portion is greater than the weight percent of the manganese in the second dopant portion.

7. The particulate metal oxide of claim 1 wherein the manganese in the second dopant portion is divalent.

8. The particulate metal oxide of claim 1 wherein the manganese in the second dopant portion is divalent and the iron dopant portion is divalent.

9. The particulate metal oxide of claim 1 wherein the manganese in the second dopant portion is divalent and the first iron dopant portion is trivalent.

10. The particulate metal oxide of claim 1 wherein the manganese dopant portion is divalent, the copper dopant portion is divalent, and the first iron dopant portion is divalent.

11. The particulate metal oxide of claim 1, wherein the cationic portion consists essentially of the zinc portion, the first iron dopant portion and the second dopant portion consisting of manganese and copper.

12. A sunscreen composition comprising a cosmetically acceptable carrier and the particulate metal oxide of claim 1.

* * * * *